United States Patent
Walsh et al.

(10) Patent No.: US 7,302,858 B2
(45) Date of Patent: Dec. 4, 2007

(54) MEMS CAPACITIVE CANTILEVER STRAIN SENSOR, DEVICES, AND FORMATION METHODS

(76) Inventors: Kevin Walsh, 205 Mockingbird Gardens Dr., Louisville, KY (US) 40207; Mark Crain, 6420 Meadow Oak Dr., Georgetown, IN (US) 47122; William Hnat, 3831 Dogwood Rd., Floyd Knobs, IN (US) 47119; Douglas Jackson, 63 Arbor Pl., New Albany, IN (US) 47190; Ji-Tzuoh Lin, 1507 S. 4th St., #2, Louisville, KY (US) 40208; John Naber, 6803 Hunters Run Pl., Prospect, KY (US) 40059

( * ) Notice: Subject to any disclaimer, the term of this patent is extended or adjusted under 35 U.S.C. 154(b) by 0 days.

(21) Appl. No.: 10/949,723

(22) Filed: Sep. 24, 2004

(65) Prior Publication Data

US 2006/0070451 A1    Apr. 6, 2006

(51) Int. Cl.
    *G01B 7/16*  (2006.01)
(52) U.S. Cl. ..................................... 73/780
(58) Field of Classification Search ............... 73/780
    See application file for complete search history.

(56) References Cited

U.S. PATENT DOCUMENTS

| | | | |
|---|---|---|---|
| 5,659,195 A * | 8/1997 | Kaiser et al. | 257/415 |
| 6,127,744 A * | 10/2000 | Streeter et al. | 307/125 |
| 6,201,629 B1 * | 3/2001 | McClelland et al. | 359/223 |
| 6,667,725 B1 * | 12/2003 | Simons et al. | 343/895 |
| 6,744,338 B2 * | 6/2004 | Nikitin | 333/262 |
| 6,835,587 B2 * | 12/2004 | Kubena et al. | 438/48 |
| 6,909,589 B2 * | 6/2005 | Huff | 361/281 |
| 6,930,368 B2 * | 8/2005 | Hartwell et al. | 257/418 |
| 2003/0220556 A1 * | 11/2003 | Porat et al. | 600/407 |
| 2004/0011137 A1 * | 1/2004 | Hnat et al. | 73/789 |
| 2006/0052782 A1 * | 3/2006 | Morgan et al. | 606/60 |

OTHER PUBLICATIONS

K.I. Arshak, D. McDonagh, M.A. Durcan, "Development of New Capacitive Strain Sensors Based on Thick Film Polymer and Cermet Technologies", Sensors and Actuators, vol. 79, 2000, pp. 102-114.

(Continued)

*Primary Examiner*—Max Noori
(74) *Attorney, Agent, or Firm*—Frost Brown Todd LLC

(57) ABSTRACT

An embodiment of the invention provides a MEMS cantilever strain sensor. Capacitor plates in a MEMS device of the invention are carried on cantilevered opposing micro-scale plates separated by a micro-scale gap under an unstrained condition. At least one of the micro-scale plates may be attached to a substrate or forms a substrate, which may be part of a monitored system. When a load is applied to the substrate, distal ends of the opposing cantilevered micro-scale plates become further separated, resulting in a change of capacitance. The change of capacitance is proportional to a load and therefore is an indication of the strain. Electrodes may be integrated into the strain sensor to provide a connection to measurement circuitry, for example. Sensors of the invention also provide for telemetric communication using radio frequency (RF) energy and can be interrogated without a power supply to the sensor.

15 Claims, 3 Drawing Sheets

OTHER PUBLICATIONS

A. DeHennis, K.D. Wise, "A Passive-Telemetry-Based Pressure Sensing System", Solid-State Sensor, Actuator and Microsystems Workshop, Hilton Head Island, South Carolina, Jun. 2-6, 2002, pp. 165-168.

M. Kanayama, B.W. Cunningham, J.C. Weis, L.M. Parker, K. Kaneda, P.C. McAfee, "Maturation of the Posterolateral Spinal Fusion and Its Effect on Load-Sharing of Spinal Instrumentation: An In Vivo Sheep Model", Bone Joint Surg. Am., vol. 79-A(11), Nov. 1997, pp. 1710-1720.

* cited by examiner

MEMS CAPACITIVE CANTILEVER STRAIN SENSOR, DEVICES, AND FORMATION METHODS

STATEMENT OF GOVERNMENT INTEREST

This invention was made with government assistance provided by the National Science Foundation under Contract No. BES-0097521. The government has certain rights in this invention.

FIELD OF THE INVENTION

A field of the invention is sensing. Another field of the invention is MEMS (micro electro mechanical systems).

BACKGROUND OF THE INVENTION

Sensors play an important role in a wide variety of devices as sensors can provide critical information concerning the status, operational conditions, performance, wear, safety, and countless other conditions. Strain sensors provide information about a load. Strain sensing can be useful as feedback in complex control systems, for example, in vehicles, roads, buildings, tools, and electronic systems, as only a few examples. Strain sensors also have a wide variety of applications in the safety systems. Load distributions provide information about the forces within a mechanical structure, including bending and twisting, that can be communicated to a monitoring device and provide warnings or historical performance information concerning the safety of a mechanical component to which a strain sensor is attached. Additionally, a strain sensor may be incorporated into an electronic control system that limits some form of operation or applies a corrective load when dangerous conditions are detected by a strain sensor. Limitations of conventional strain sensors include the power consumption needs of the strain sensors, the manner in which the strain sensors may be connected into other systems, and the size of the strain sensors.

SUMMARY OF THE INVENTION

An embodiment of the invention provides a MEMS cantilever strain sensor. Capacitor plates in a MEMS device of the invention are carried on cantilevered opposing micro-scale plates separated by a micro-scale gap under an unstrained condition. At least one of the micro-scale plates may be attached to a substrate or forms a substrate, which may be part of a monitored system. When a load is applied to the substrate, distal ends of the opposing cantilevered micro-scale plates become further separated, resulting in a change of capacitance. The change of capacitance is proportional to a load and therefore is an indication of the strain. Electrodes may be integrated into the strain sensor to provide a connection to measurement circuitry, for example. Sensors of the invention also provide for telemetric communication using radio frequency (RF) energy and can be interrogated without a power supply to the sensor. In other embodiments, power is supplied directly to a strain sensor of the invention and control circuitry, such as through a battery. Strain sensors of the invention may be packaged in any number of physical packages, such as glass, plastic, and including biologically compatible packages. Sensors of the invention provide highly compact, MEMS scale, and very low power strain sensor devices. A particular exemplary device including a strain sensor of the invention is a spinal fusion system including a strain sensor. The invention also includes fabrication methods for production of strain sensors of the invention.

DETAILED DESCRIPTION

Figure 1A:
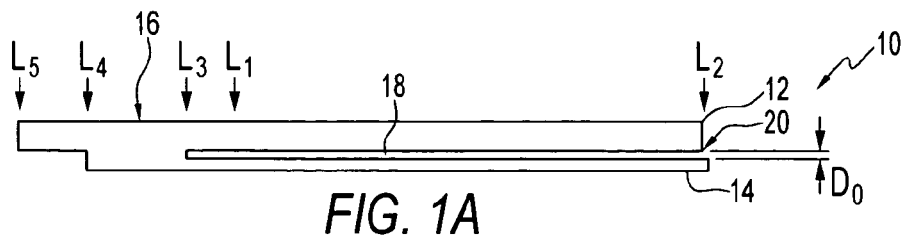
FIG. 1A is a schematic view of a MEMS strain sensor in accordance with an embodiment of the invention in an unstrained condition.

The invention provides a MEMS capacitive cantilever strain sensor. A sensor of the invention may monitor the mechanical strain of a member to which the sensor is attached, or a member to be monitored can comprise the substrate of a sensor of the invention. The value of capacitance between the opposing cantilever micro-scale plates of the invention varies under load conditions. A variable capacitor is thus produced whose capacitance depends on the load supplied. Devices of the invention may be formed from a variety of materials, including semi-conductor materials, glass, and plastics. Any dielectric material or a material that can be treated to have dielectric qualities and that can be fabricated by MEMS processing techniques can be used as the basis for the cantilever structure in a MEMS strain sensor of the invention, so long as a conductive material can be formed on the opposing surfaces of the dielectric opposing cantilever micro-scale plates.

Exemplary MEMS cantilever strain sensors of the invention interface with circuits through an electrode connection, which might also form part of the inner connection pattern for a circuit into which the MEMS cantilever strain sensor of the invention is incorporated. MEMS strain sensors in exemplary embodiments of the invention can provide high gauge factors, for example, between 250 and 1000, far exceeding the gauge factors of conventional metal foil and piezoresistive strain sensors. Also, because capacitance is relied upon for sensing an amount of strain, devices of the invention are particularly well-suited for low power applications, including those using battery power sources. In addition, devices of the invention may be interrogated via RF energy, and devices of the invention are implantable in both inanimate and biologic hosts. Artisans will appreciate an even wider variety of application for MEMS cantilever strain sensors of the invention, as the above provides mere outline of some particular preferred example applications.

Artisans will appreciate additional features and applications of the invention from reading the following description of some preferred embodiments with reference to the attached drawings. The attached drawings are not to scale, and no proportions may be assumed in the attached drawings. Features may be exaggerated for purpose of illustration, and the schematic views presented in the drawings will be understood by artisans as such views are commonly used in the art. Micro-scale, as used herein, refers general to the dimensions achieved by microfabrication processes well-known to artisans in the MEMS community.

Figure 1B:
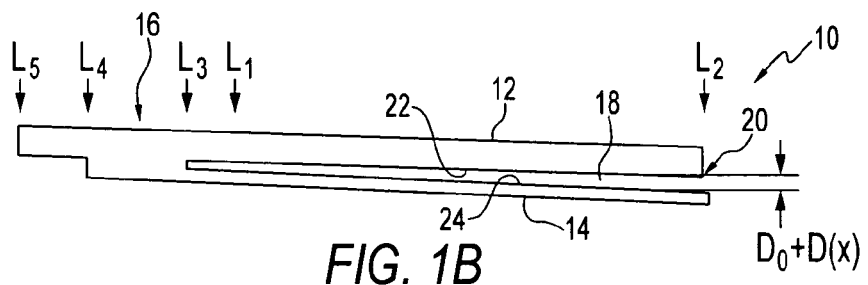
FIG. 1B is a schematic side view of the FIG. 1A MEMS strain sensor under a strained condition.
Figure 1C:
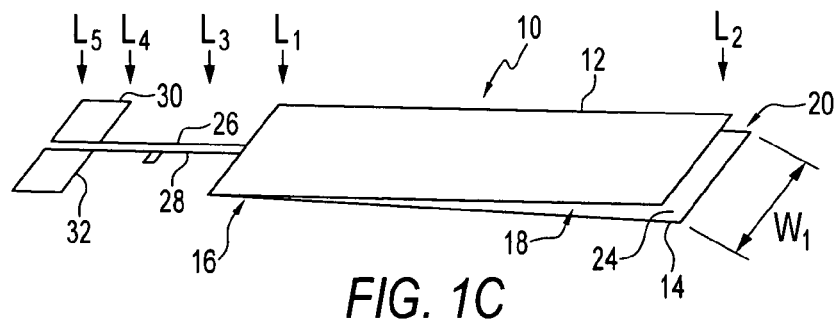
FIG. 1C is a schematic perspective view of FIGS. 1A and 1B MEMS strain sensor under the strained condition of FIG. 1B.

Referring now to FIGS. 1A-1C, an exemplary embodiment MEMS cantilever strain sensor 10 is shown. The strain sensor 10 includes opposing cantilever micro-scale plates 12, 14. The cantilevered micro-scale plates 12, 14 are bonded together or formed from a common unitary structure connected at a cantilever end 16 and are separated by a gap 18 at a distal end 20. Conductive capacitor plate material is carried on opposing surfaces 22, 24 of the micro-scale plates 12 and 14 within the gap 18. Leads 26, 28 connect the conductive material on the opposing surfaces 22, 24 to electrodes 30, 32.

In FIG. 1A, the MEMS cantilever strain sensor 10 is under a condition of no loading, i.e., loads $L_1$ through $L_5$ are equal to zero. Under zero load, the gap 18 creates a separation $D_0$ between the distal end 20 of the opposing micro-scale plates 12, 14. When loading is applied as shown in FIGS. 1B and 1C, the gap 18 at the distal end 20 increases to a distance $D_0+D(x)$. At the distal end 20 there is a mechanical amplification effect of the bending strain applied uniformly across the plate 12. The plate 12 may be fixed to a member that provides the load forces $L_1$ through $L_5$ under particular conditions or the plate 12 may be part of a member that undergoes load forces $L_1$ through $L_5$ under particular conditions. The capacitance is a function of the distance $D_0+D(x)$, and the surface area determined by the length and the width $W_1$ of the conductive material formed on the opposing surfaces 22, 24.

Figure 1D:
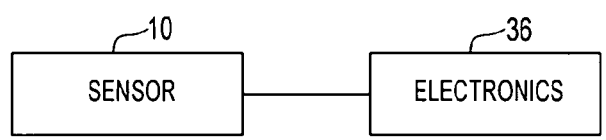
FIG. 1D is a block diagram of a sensor system in accordance with an embodiment of the invention.
Figure 1E:
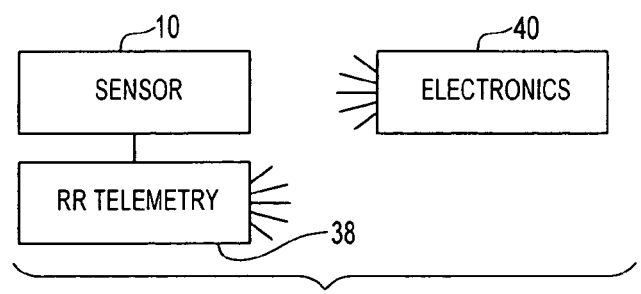
FIG. 1E is a block diagram of a sensor system in accordance with another embodiment of the invention.

As is known in the MEMS industry, MEMS devices may be integrated on a substrate along with electronics. FIG. 1D shows an exemplary schematic wherein a sensor 10 is connected to interrogation electronics 36 through a direct electrical connection, which may be a circuit interconnect pattern, electrodes, wire bond pads, etc. Additionally, because of the capacitive nature of the sensing, with integrated RF telemetry circuitry 38, in a suitable package, electronics with RF capability 40 may interrogate the sensor 10 in a battery-free inquiry similar to the manner in which radio frequency identification (RFID) inquires are made to RFID devices.

Figure 2A:
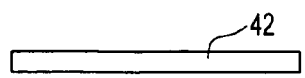
FIGS. 2A-2O are schematic diagrams illustrating a method for fabricating a MEMS strain sensor in accordance with an embodiment of the invention.
Figure 2B:
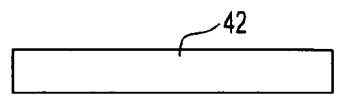
Figure 2C:
Figure 2D:
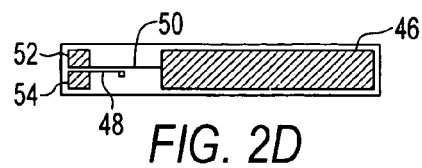
Figure 2E:
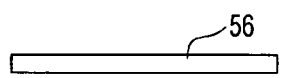
Figure 2F:
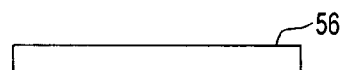
Figure 2G:
Figure 2H:
Figure 2I:
Figure 2J:
Figure 2K:
Figure 2L:
Figure 2M:
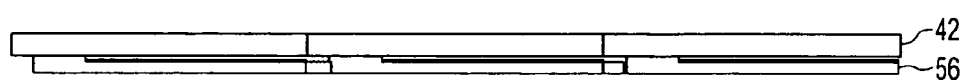
Figure 2N:
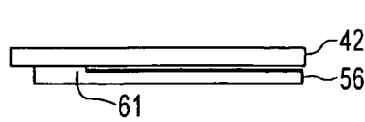
Figure 2O:
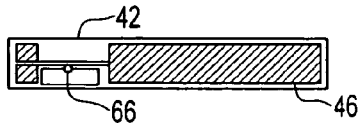

An example fabrication method is shown in FIGS. 2A through 2O. In FIG. 2A, an exemplary fabrication process will be described wherein the separate opposing micro-scale plates of an example MEMS cantilever strain sensor are formed from different materials such as might be used in a packaging of the MEMS cantilever strain sensor. It is possible, of course, to form the opposing micro-scale plates from the same material. It is also possible, to form a generally unitary structure by multiple deposit steps and the formation and release of a sacrificial layer in the gap of the sensor. FIGS. 2A and 2B show a substrate 42. FIG. 2A is a side view and FIG. 2B is a top view. The substrate 42 may be, for example, glass, ceramic, plastic, semi-conductor material, or another suitable material. In FIGS. 2C and 2D, a conductive layer 44 is deposited and patterned into a capacitor plate 46, leads 48, 50, and electrodes 52, 54. FIG. 2C shows the side view and FIG. 2D shows the top view. The deposition of metal may be, for example, sputter deposition.

FIGS. 2E and 2F show a second substrate, 56, for example, a semi-conductor or dielectric material. Assuming that the substrate 56 is a semi-conductor material, FIGS. 2G and 2H illustrate the formation of a dielectric interface region in the semi-conductor material, for example, by oxidation of a layer of silicon if the substrate is a silicon substrate to form silicone dioxide. The dielectric layer 58 is best seen in the side view of FIG. 2G.

A material removal process, e.g., etching, forms a patterned plane 60 below the level of a mesa 61 on the second substrate 56. The different level of the mesa 61 and the plane 60 will provide the capacitive gap between micro-scale plates of the MEMS strain sensor. The shape of the plane 60 is best seen in the top view of FIG. 2J, while the depth of the plane 60 is represented in FIG. 2I. The depth of the plane 60 leaves sufficient dielectric 58 to provide electrical insulation from a second capacitor plate 62 that is formed by a metal deposit as shown in FIGS. 2K and 2L. The metal deposit also results in a lead 64 and contact pad 66, the contact pad 66 extending onto the mesa 61 above the level of the plane 60 so that the contact pad 66 may make contact with the lead 48 that is formed on the substrate 42 as a result of the bonding depicted in FIG. 2M.

While a single structure is described as being formed, in practice the steps will be carried out on a large scale using two substrates having the above processes carried out on different areas of the substrates. Bonding and dicing, seen in FIG. 2M, then results in a plurality of individual MEMS cantilever strain sensors, one of which is shown in FIG. 2N. If the substrate 42 is transparent plastic or glass, the top view will show the capacitive plate 46 as seen in the top view of FIG. 2O.

As with other MEMS devices, a MEMS cantilever strain sensor of the invention may be conveniently packaged and integrated with other electronic systems. Substrates used to form cantilever micro-scale plates may be selected to suit particular packaging arrangements. An example application will now be discussed to provide a sample of the potential for use of the strain sensor in a biological environment.

Figure 3:
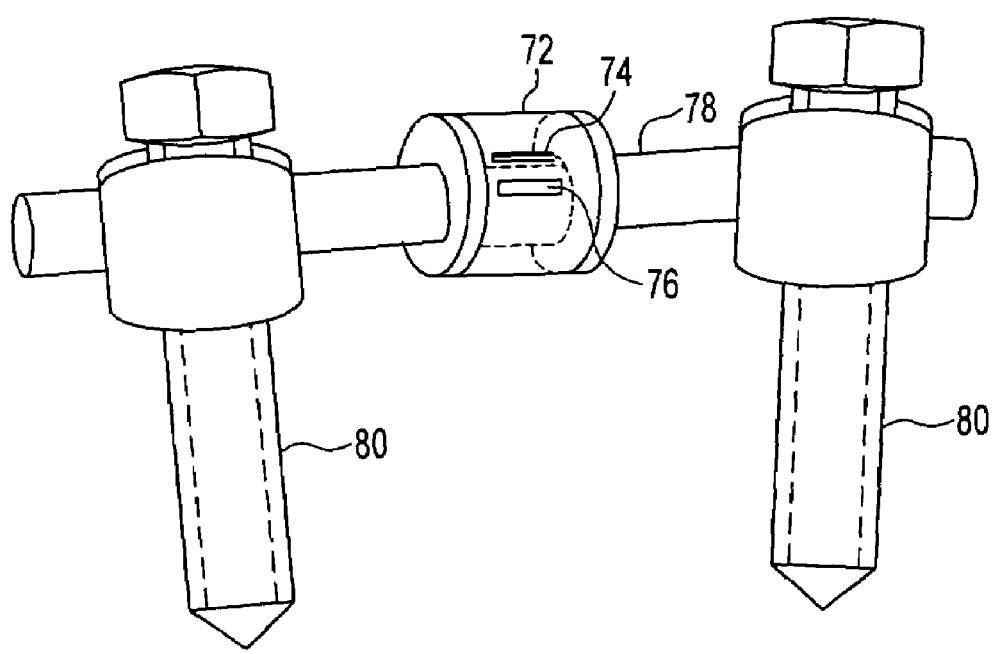
FIG. 3 illustrates a spinal fusion system in accordance with an embodiment of the invention.

FIG. 3 shows an exemplary spinal fusion surgery device including an integrated MEMS cantilever strain sensor. A housing 72 houses a strain sensor 74 and a sensing circuit 76. The housing 76 is formed of a biologically compatible material, such as polymers typically used in such applications, and the strain sensor 74 is attached to a spinal fusion rod 78 in a manner such that the MEMS cantilever strain sensor 74 can detect a load on the spinal fusion rod 78. Pedical screws 80 are for attachment into vertebrae and connect the spinal fusion rod 78, where the spinal fusion rod provides support to connect vertebrae. The rod and screws are typically made of titanium or stainless steel rods and serve to stabilize vertebrae movement, allowing fusion of the spine to occur over time.

A typical method for monitoring the fusion process after operation includes CAT scans and magnetic resonance imaging, but the results from these procedures are subjective and fail to provide real time analysis. These procedures also have significant expense associated with them. The strain sensor 74 and circuit 76 provide an alternate approach for monitoring the spinal fusion process. After implantation into a patient's body, the load on the rod 78 is gradually transferred to the bone as the bone graft heals, resulting in a decrease of the load on the rod 78 over time. The capacitance of the sensor 74 will therefore change as the gap narrows between opposing capacitor micro-scale plates. The circuit 76 may comprise sensing circuitry, telemetry circuitry, and an antenna, and the amount of strain therefore may be interrogated using an inductively coupled battery-free method similar to radio frequency identification. Exemplary gaps in the approximate range of 3 to approximately 10 micrometers have been modeled to provide sensitivity to a 1,000 micro strain, which can be interrogated by a low power capacitance to frequency converter in the circuit 76 that may be interrogated by a powered reader that subjects the circuit 76 to RF frequencies. Successful results have been achieved in cadaver testing.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the following claims.

The invention claimed is:

1. A MEMS strain sensor, the sensor comprising:
opposing micro-scale plates, separated at a distal end and over at least a substantial portion of opposing surfaces of said micro-scale plates by a micro-scale gap;
said opposing micro-scale plates being joined or unitary at another end opposite said distal end;
capacitive plates carried on said opposing surfaces and electrically isolated from each other by said micro-scale gap;
leads from each of said capacitive plates; and
a circuit connected to said leads;
wherein said circuit comprises a radio telemetry circuit.

2. The sensor of claim 1, wherein said opposing micro-scale plates are joined by bonding at said another end.

3. The sensor of claim 1, wherein said plates comprise dielectric material.

4. The sensor of claim 1, wherein one of said micro-scale plates comprises a semiconductor including a dielectric region that carries one of said capacitive plates.

5. A MEMS strain sensor, the sensor comprising:
a first micro-scale plate;
a second micro-scale plate bonded to said first micro-scale plate at one end and shaped by micro-fabrication to define a micro-scale separation from said first micro-scale plate at a distal end and over substantial opposing surfaces of said first and second micro-scale plates;
a first metal layer carried on one of said opposing surfaces;
a second metal layer carried on another one of said opposing surfaces; and
a housing shaped to receive a surface subject to deflection under a strain load and alignedly attached to a selected one of the first and second micro-scale plates to communicate the deflection in relation to the strain load.

6. The sensor of claim 5, wherein said first micro-scale plate comprises glass or plastic.

7. A MEMS strain sensor, the sensor comprising:
opposing micro-scale plates, separated at a distal end and over at least a substantial portion of opposing surfaces of said micro-scale plates by a micro-scale gap;
said opposing micro-scale plates being joined or unitary at another end opposite said distal end;
capacitive plates carried on said opposing surfaces and electrically isolated from each other by said micro-scale gap;
wherein one of said opposing plates is attached directly or eventually to a load applying member, said load applying member comprising a rod, said rod being joined to pedical screws for bearing load from said pedical screws.

8. The sensor of claim 6, wherein said second micro-scale plate comprises a semiconductor.

9. The sensor of claim 5, wherein said housing is formed of a biologically compatible material.

10. The sensor of claim 9, wherein said housing comprises a polymer housing.

11. A spinal support structure, comprising:
pedical screws;
a support rod connecting said pedical screws;
a MEMS cantilever strain capacitive sensor attached to said rod to accept loading from said rod and produce variable capacitor response;
a radio telemetry circuit for reading said variable capacitor response; and
a biologically compatible housing houses said MEMS cantilever strain sensor and said radio telemetry circuit.

12. A spinal support structure, comprising:
pedical screws;
a support rod connecting said pedical screws;
a MEMS cantilever strain sensor, comprising:
opposing micro-scale plates, separated at a distal end and over at least a substantial portion of opposing surfaces of said micro-scale plates by a micro-scale gap,
said opposing micro-scale plates being joined or unitary at another end opposite said distal end,
capacitive plates carried on said opposing surfaces and electrically isolated from each other by said micro-scale gap,
leads from each of said capacitive plates, and
a circuit connected to said leads,
the MEMS strain sensor being attached to said rod to accept loading from said rod and produce variable capacitor response;
a radio telemetry circuit for reading said variable capacitor response; and
a biologically compatible housing houses said MEMS cantilever strain sensor and said radio telemetry circuit.

13. The sensor of claim 7, wherein said opposing micro-scale plates are joined by bonding at said another end.

14. The sensor of claim 7, wherein said plates comprise dielectric material.

15. The sensor of claim 7, wherein one of said micro-scale plates comprises a semiconductor including a dielectric region that carries one of said capacitive plates.

* * * * *